(12) United States Patent
Uchimoto et al.

(10) Patent No.: US 8,686,217 B2
(45) Date of Patent: Apr. 1, 2014

(54) ABSORBENT PRODUCT

(75) Inventors: Kenichi Uchimoto, Osaka (JP); Yasuji Yasumitsu, Kochi (JP)

(73) Assignee: Livedo Corporation, Ehime (JP)

( * ) Notice: Subject to any disclaimer, the term of this patent is extended or adjusted under 35 U.S.C. 154(b) by 11 days.

(21) Appl. No.: 13/600,434

(22) Filed: Aug. 31, 2012

(65) Prior Publication Data

US 2012/0330259 A1     Dec. 27, 2012

Related U.S. Application Data

(63) Continuation of application No. 12/155,806, filed on Jun. 10, 2008, now Pat. No. 8,329,978.

(30) Foreign Application Priority Data

Jun. 22, 2007    (JP) ................ P2007-164672

(51) Int. Cl.
     *A61F 13/15*      (2006.01)

(52) U.S. Cl.
     USPC ........... 604/372; 604/365; 604/368; 604/374; 604/375; 604/378; 604/385.101

(58) Field of Classification Search
     USPC ................. 604/372, 367, 368, 374, 375, 378, 604/385.01
     See application file for complete search history.

(56) References Cited

U.S. PATENT DOCUMENTS

| | | | |
|---|---|---|---|
| 5,562,646 A | 10/1996 | Goldman et al. | |
| 5,693,037 A | 12/1997 | Lee et al. | |
| 5,994,615 A | 11/1999 | Dodge, II et al. | |
| 6,224,961 B1 | 5/2001 | Hsueh et al. | |
| 6,296,862 B1 | 10/2001 | Paul et al. | |
| 6,441,266 B1 | 8/2002 | Dyer et al. | |
| 6,548,731 B2 | 4/2003 | Mizutani et al. | |
| 6,646,180 B1 | 11/2003 | Chmielewski | |
| 2001/0014797 A1 | 8/2001 | Suzuki et al. | |
| 2001/0026858 A1 | 10/2001 | Takai et al. | |
| 2003/0068467 A1 | 4/2003 | Takai et al. | |
| 2007/0116926 A1 | 5/2007 | Hoying et al. | |

FOREIGN PATENT DOCUMENTS

| | | |
|---|---|---|
| CN | 1184413 | 6/1998 |
| CN | 1318355 | 10/2001 |
| CN | 1329881 | 1/2002 |
| EP | 0254 393 | 4/1987 |

(Continued)

OTHER PUBLICATIONS

Chinese Office Action issued Jan. 26, 2011 in corresponding Chinese Application No. 200810111466, with English translation.

(Continued)

*Primary Examiner* — Jacqueline F. Stephens
(74) *Attorney, Agent, or Firm* — Wenderoth, Lind & Ponack, L.L.P.

(57) ABSTRACT

An absorbent product has a top sheet, an absorbent core and a back sheet. The absorbent core includes 40% by weight or more of high absorbent resin powder and it is possible to slim down the absorbent core while keeping a sufficient amount of absorption to thereby achieve slimming down of the absorbent product. A top sheet lower part contacting the high absorbent resin powder in the absorbent core includes hydrophilic fibers having water retention characteristics, and moisture is temporarily retained in the top sheet lower part before reaching the absorbent core and rapidly disperses in a range facing the absorbent core of the top sheet lower part. As a result, it is possible to reliably absorb the moisture of excrement in the absorbent core and to simplify a structure of the absorbent product.

11 Claims, 4 Drawing Sheets

(56) References Cited

FOREIGN PATENT DOCUMENTS

| | | |
|---|---|---|
| EP | 0 235 309 | 9/1987 |
| EP | 0 945 537 | 9/1999 |
| EP | 1 060 722 | 12/2000 |
| JP | 61-125343 | 6/1986 |
| JP | 61-141361 | 6/1986 |
| JP | 8-66425 | 3/1996 |
| JP | 08-246321 | 9/1996 |
| JP | 2001-46435 | 2/2001 |
| JP | 2001-145648 | 5/2001 |
| JP | 2004-166832 | 6/2004 |
| JP | 2005-319043 | 11/2005 |
| JP | 2006-239127 | 9/2006 |
| WO | 01/54640 | 8/2001 |

OTHER PUBLICATIONS

Notice of Opposition issued May 18, 2012 in corresponding European Application No. 08010613.1.

II - II

ABSORBENT PRODUCT

This application is a Continuation of U.S. application Ser. No. 12/155,806, filed Jun. 10, 2008 now U.S. Pat. No. 8,329,978.

BACKGROUND OF THE INVENTION

1. Field of the Invention

The present invention relates to an absorbent product for receiving excrement from a wearer.

2. Description of the Background Art

In an absorbent product such as a disposal diaper, conventionally, an absorbent core which is formed by sandwiching crushed pulp and high absorbent resin powder between tissue papers, nonwoven fabrics or the like has been used for absorbing moisture such as urine. Recently, a thin absorbent core where high absorbent resin powder is bonded on a base sheet such as a nonwoven fabric is used; for example, International Patent Publication No. WO 01/54640 (Document 1) discloses a disposal wearing product having a sheet-like absorbent where a layer of highly water absorbing composite composition which is made of micro-fibrillated cellulose and highly water absorbing resin (highly absorbing resin), is partly bonded on a nonwoven fabric support.

In such a thin absorbent not using the crushed pulp, since the absorption speed of the highly water absorbing resin is lower than that of the crushed pulp, if a wearer urinates greatly or the like, there is a possibility that large amounts of urination concentrates on a portion close to a urination portion of the absorbent, absorption of the urination is delayed and leak of urine from an absorbent product occurs.

In Document 1, a technique for preventing concentration of much moisture over an absorption speed of the sheet-like absorbent on a part of the sheet-like absorbent, where the layer of the highly water absorbing composite composition in the sheet-like absorbent is provided on a lower surface of the nonwoven fabric support (the lower surface being opposed to a top sheet), a bulky and thick temporal water-storage layer made of nonwoven fabric whose weight per unit area is 20 to 100 g/m² is provided between the top sheet and the nonwoven fabric support in the sheet-like absorbent, and thereby, moisture such as urine penetrates to the sheet-like absorbent while dispersing in a planar direction of the temporal water-storage layer. It is possible to make full use of the ability of absorption of the sheet-like absorbent and to prevent leak of urine or the like.

Japanese Patent Application Laid-Open No. 2006-239127 (Document 2) discloses a technique for using a diffusion sheet for an absorbent as a surface sheet (top sheet) of an absorbent product, the diffusion sheet is formed by laminating a thin fineness layer and a thick fineness layer and integrating them by thermal bonding. The thin fineness layer and the thick fineness layer include thermoplastic composite fibers (e.g., polyolefin composite fibers or polyamide composite fibers), and hydrophilic treatment by hydrophilic oil is preferably performed on the thermoplastic composite fibers included in the both layers. In the diffusion sheet of Document 2, body fluid discharged from a wearer rapidly moves to the thick fineness layer by the thin fineness layer, passes through the thick fineness layer to an absorption layer positioned on a lower surface of the diffusion sheet while moving (i.e., dispersing) along the thermoplastic composite fibers in the thick fineness layer in a horizontal direction. Water-repellent fibers are included in the thick fineness layer as well as the thermoplastic composite fibers, in order to suppress moving back of the body fluid which has reached the absorption layer to the wearer, caused by body pressure or the like.

The disposal wearing product of Document 1 is slimmed down as compared with the absorbent product having the absorbent core using the crushed pulp, however, the temporal water-storage layer is bulky and thick and there is a limitation in slimming down of the disposal wearing product. Since the temporal water-storage layer, which is a separated member from the top sheet and the sheet-like absorbent, is provide between the top sheet and the sheet-like absorbent, the structure of the disposal wearing product is complicated and there is a possibility that the manufacturing cost of the disposal wearing product is increased.

In the diffusion sheet of Document 2, the thermoplastic composite fibers with the hydrophilic treatment is used for dispersing moisture in the thick fineness layer and it is not considered that a certain amount of moisture is temporally retained in the thick fineness layer. Therefore, in a case where large amounts of urine or the like is discharged, even if moisture disperses in the thick fineness layer, it is thought much moisture over an absorption speed of the absorption layer moves from the diffusion sheet to the absorption layer in a diffusion range and there is a possibility that leak from the absorbent product occurs.

SUMMARY OF THE INVENTION

The present invention is intended for an absorbent product for receiving excrement from a wearer. It is an object of the present invention to achieve slimming down of the absorbent product and simplification of a structure of the absorbent product, and to reliably absorb moisture of the excrement.

The absorbent product comprises: an absorbent core which includes 40% by weight or more of high absorbent resin powder; a top sheet which is made of nonwoven fabric covering an upper surface of the absorbent core; and a back sheet covering a lower surface of the absorbent core, and in the absorbent product, the top sheet comprises: a top sheet lower part which contacts with the high absorbent resin powder included in the absorbent core and includes hydrophilic fibers having water retention characteristics, the hydrophilic fibers being natural fibers and/or regenerated fibers; and a top sheet upper part which is positioned on the top sheet lower part, a ratio of the hydrophilic fibers by weight in the top sheet upper part being lower than that in the top sheet lower part.

In the absorbent product, since the absorbent core includes 40% by weight or more of the high absorbent resin powder, it is possible to achieve slimming down of the absorbent product while keeping a sufficient amount of absorption. The top sheet lower part contacts the high absorbent resin powder and includes the hydrophilic fibers and thereby, moisture such as urine is temporarily retained and rapidly disperses in the top sheet lower part. As a result, it is possible to reliably absorb moisture of excrement in the absorbent core and to achieve simplification of a structure of the absorbent product. Since a ratio of the hydrophilic fibers by weight in the top sheet upper part is lower than that in the top sheet lower part, it is hard for moisture to be temporarily retained in the top sheet upper part as compared with the top sheet lower part and it is possible to improve the feel of the absorbent product.

According to a preferred embodiment of the present invention, a ratio of the hydrophilic fibers included in the top sheet lower part is equal to or larger than 25% by weight and equal to or smaller than 40% by weight.

According to another preferred embodiment of the present invention, a ratio of the hydrophilic fibers included in the top sheet upper part is equal to or smaller than 15% by weight. Or, the top sheet upper part is made of only hydrophobic fibers which are synthetic fibers.

According to still another preferred embodiment of the present invention, the top sheet is a laminated body of a plurality of nonwoven fabrics, the top sheet lower part includes a lowest nonwoven fabric of the plurality of nonwoven fabrics, and the top sheet upper part includes an uppermost nonwoven fabric of the plurality of nonwoven fabrics. More preferably, the top sheet is a laminated body of two nonwoven fabrics. It is also preferable that the lowest nonwoven fabric of the top sheet is formed by an air-laying method, and more preferably, the plurality of nonwoven fabrics are formed by the air-laying method.

According to still another preferred embodiment of the present invention, the absorbent core comprises: a sheet-like supporting member; and the high absorbent resin powder bonded on a main surface of the supporting member, the main surface being opposed to the top sheet. More preferably, the high absorbent resin powder is applied on the supporting member in stripe pattern. It is preferable that a weight per unit area of the supporting member in the absorbent core is equal to or larger than 10 $g/m^2$ and equal to or smaller than 100 $g/m^2$.

These and other objects, features, aspects and advantages of the present invention will become more apparent from the following detailed description of the present invention when taken in conjunction with the accompanying drawings.

DETAILED DESCRIPTION OF THE INVENTION

Figure 1:
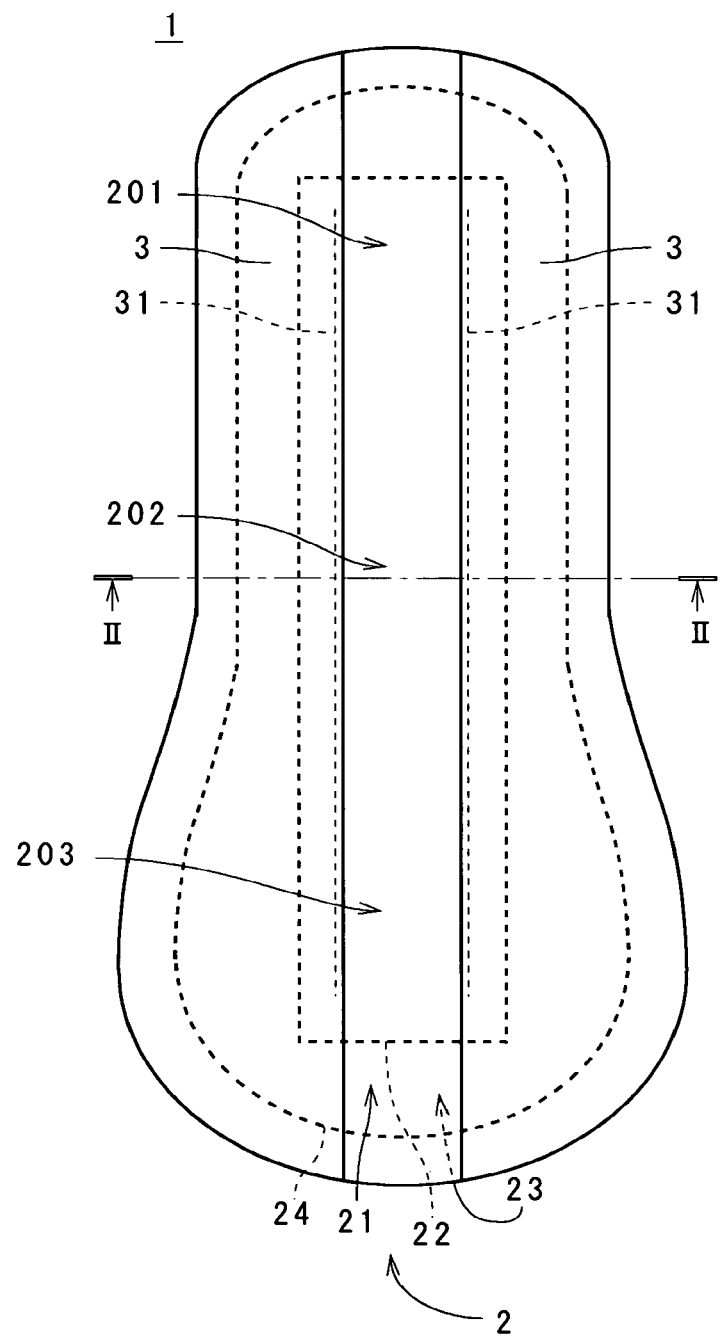
FIG. 1 is a plan view of an absorbent product in accordance with the first preferred embodiment.
Figure 2:
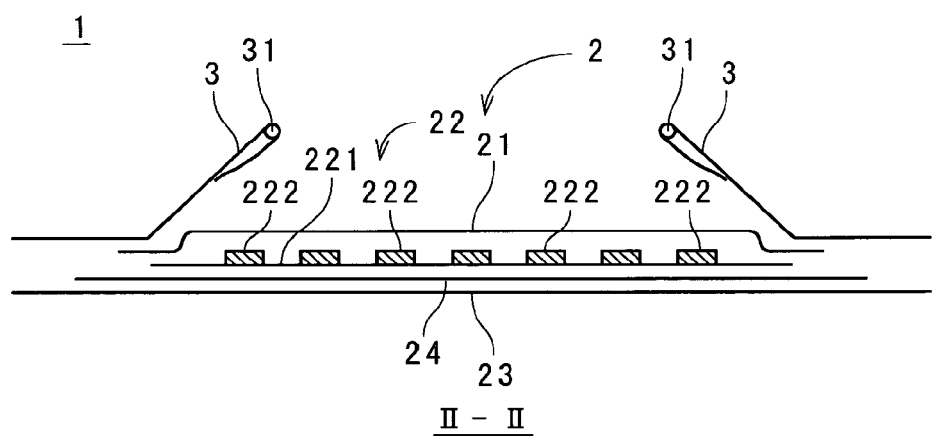
FIG. 2 is a cross-sectional view of the absorbent product.

FIG. 1 is a plan view showing an absorbent product 1 in accordance with the first preferred embodiment of the present invention, and FIG. 2 is cross-sectional view of the absorbent product 1 taken along a plane perpendicular to a longitudinal direction (i.e., vertical direction in FIG. 1) at the positions indicated by the arrows II-II shown in FIG. 1. The absorbent product 1 is a thin auxiliary absorbent pad which is attached on an inner side of underpants, a disposal diaper or the like which are exterior products of wearer, for receiving excrement such as urine from the wearer (the auxiliary absorbent pad is a so-called incontinence pad). In FIG. 1, the absorbent product 1 is shown in a state where a surface on an inner side of the absorbent product 1 is put on a viewer's side. In FIG. 2, constituent elements of the absorbent product 1 are apart from one another for convenience of illustration (the same is applied in FIG. 5).

In the absorbent product 1, a portion on the upper side of FIG. 1 is a front part 201 to be positioned on the stomach side of the wearer and a portion on the lower side of FIG. 1 is a back part 203 to be positioned on the back side of the wearer. A portion between the front part 201 and the back part 203 is a middle part 202 to come into contact with a crotch region of the wearer. In the present preferred embodiment, the width of the back part 203 is larger than that of the front part 201 and the middle part 202, and fitting of the absorbent product 1 to the wearer is improved by forming an end portion in the longitudinal direction (i.e., vertical direction in FIG. 1) of the front part 201 and the whole back part 203 in the plan view, into a smooth round shape.

As shown in FIGS. 1 and 2, the absorbent product 1 has an almost sheet-like main body part 2 and a pair of side wall parts 3 which are provided over an almost entire length in the longitudinal direction of the main body part 2 on right and left sides in a width direction perpendicular to the longitudinal direction. An elastic member 31 extending in the longitudinal direction is bonded on each of the pair of side wall parts 3, and the elastic members 31 are extended in a state where the absorbent product 1 is expanded (see FIG. 1). In the absorbent product 1, the side wall parts 3 stand up toward the wearer on the right and left sides of the main body part 2 by contracting the elastic members 31, and gathers which come into contact with the vicinity of wearer's crotch in wearing are formed to thereby prevent leak of urine or the like from the side wall parts 3.

The side wall parts 3 are made of water-repellent or liquid-impervious nonwoven fabric (i.e., spunbond nonwoven fabric, meltblown nonwoven fabric, or SMS (spunbond-meltblown-spunbond) nonwoven fabric) which are made of hydrophobic synthetic fibers, plastic film with no hole, plastic film with fine holes, or combinations of these materials. From the viewpoint of improving comfort of the absorbent product 1, it is preferable that the side wall parts 3 have breathability and a permeable plastic film is used as a plastic film. In the present preferred embodiment, water-repellent nonwoven fabric made of hydrophobic synthetic fibers is used for making the side wall parts 3.

The elastic members 31 are made of elastic material such as polyurethane synthetic rubber, styrene synthetic rubber or natural rubber which are formed into yarn-like, sheet-like (i.e., strip-like) or non-woven fabric form. The elastic member 31 is bonded with each of the side wall parts 3 by hot melt adhesive, thermo compression bonding, ultrasonic compression bonding or the like. In the preferred embodiment, a polyurethane yarn with a fineness of 100 to 3000 decitex (dtex) is used as the elastic member 31, and the polyurethane yarn is bonded with the side wall part 3 by using rubber hot melt adhesive in a state where the polyurethane yarn is extended five times as long as or smaller than it is. A plurality of elastic members 31 may be provided in each of the side wall parts 3.

As shown in FIGS. 1 and 2, the main body part 2 has an absorbent core 22 which is a sheet-like absorbent, a top sheet 21 covering an upper surface of the absorbent core 22 (i.e., one main surface on an inner side of the absorbent core 22), a back sheet 23 covering a lower surface of the absorbent core 22 (i.e., the other main surface of the absorbent core 22), and a mount 24 which is a sheet member overlapping with the whole absorbent core 22 between the absorbent core 22 and the back sheet 23.

As shown in FIG. 2, the side wall parts 3 are bonded with the top sheet 21, the mount 24, and the back sheet 23 on right and left sides in the width direction of the absorbent core 22, by using the hot melt adhesive or the like in the absorbent product 1. The top sheet 21 is bonded with the back sheet 23 in the vicinities of end portions in the longitudinal direction of the absorbent product 1 shown in FIG. 1.

The top sheet 21 is made of liquid-pervious nonwoven fabric, and the top sheet 21 immediately catches moisture of excrement from the wearer and moves the moisture into the absorbent core 22. The top sheet 21 is a laminated body of a plurality of nonwoven fabrics, and the top sheet 21 in the present preferred embodiment is a laminated body of two nonwoven fabrics. The structure of the top sheet 21 will be described later.

The absorbent core 22 has a sheet-like supporting member 221 made of nonwoven fabric, tissue paper or the like and high absorbent resin layers 222 provided on a main surface of the supporting member 221, the main surface being opposed to the top sheet 21. The high absorbent resin layers 222 are formed by bonding high absorbent resin powder on the main surface of the supporting member 221 with use of adhesive.

The supporting member 221 is preferably made of liquid-pervious nonwoven fabric and a nonwoven fabric whose weight per unit area is equal to or larger than 10 g/m$^2$ and equal to or smaller than 100 g/m$^2$ is used in the present preferred embodiment. For example, SAP (Super Absorbent Polymer) is used as the high absorbent resin powder forming the high absorbent resin layers 222. Examples of the adhesive for bonding the high absorbent resin powder are the hot melt adhesive, starch paste, heat-meltable fiber, cellulose microfibril and the like, and the hot melt adhesive is used in the present preferred embodiment. Since the hot melt adhesive is used as the adhesive, it is possible to easily change an application amount or an application pattern of the adhesive or a type of the adhesive, in accordance with material of the supporting member 221, a construction of a manufacturing apparatus of the absorbent product, or the like.

The high absorbent resin layers 222 (i.e., the high absorbent resin powder) are arranged (applied) on the supporting member 221 in stripe pattern extending in the longitudinal direction. In other words, an area where the high absorbent resin powder doesn't exist is provided between a plurality of high absorbent resin layers 222 extending in the longitudinal direction. The weight of the high absorbent resin powder included in the absorbent core 22 is equal to or larger than 40% (more preferably, equal to or larger than 50%) of that of the whole absorbent core 22. That is, the absorbent core 22 includes at least 40% by weight or more (more preferably, 50% by weight or more) of the high absorbent resin powder.

In the absorbent product 1, the top sheet 21 and the absorbent core 22 are bonded by the hot melt adhesive, heat sealing or the like. In the present preferred embodiment, the hot melt adhesive is intermittently applied onto the absorbent core 22 or the top sheet 21 in a spiral pattern, a fibrous pattern, a stripe pattern, a dot pattern or the like and the absorbent core 22 and the top sheet 21 are bonded with each other. Since the hot melt adhesive is intermittently applied as discussed above, it is possible to prevent absorption of moisture such as urine by the high absorbent resin powder from being interfered by the hot melt adhesive. Swelling of the high absorbent resin powder after absorbing moisture is not interfered and therefore, the high absorbent resin powder can absorb large amounts of moisture.

In the plan view shown in FIG. 1, the size of the mount 24 is slightly smaller than the back sheet 23, the shape of the mount 24 is almost same as the back sheet 23, and the contour of the mount 24 is along the back sheet 23 inside the contour of the back sheet 23. Since the mount 24 is made of material having higher rigidity than the back sheet 23, it is possible to maintain the shape of the absorbent product 1, and to prevent deformation of the absorbent product 1.

The back sheet 23 is made of water-repellent or liquid-impervious nonwoven fabric (i.e., spunbond nonwoven fabric, meltblown nonwoven fabric, or SMS nonwoven fabric) which are made of hydrophobic synthetic fibers, plastic film with no hole, plastic film with fine holes, or combinations of these materials. From the viewpoint of improving comfort of the absorbent product 1, it is preferable that the back sheet 23 has breathability and a permeable plastic film is used as a plastic film.

Figure 3:
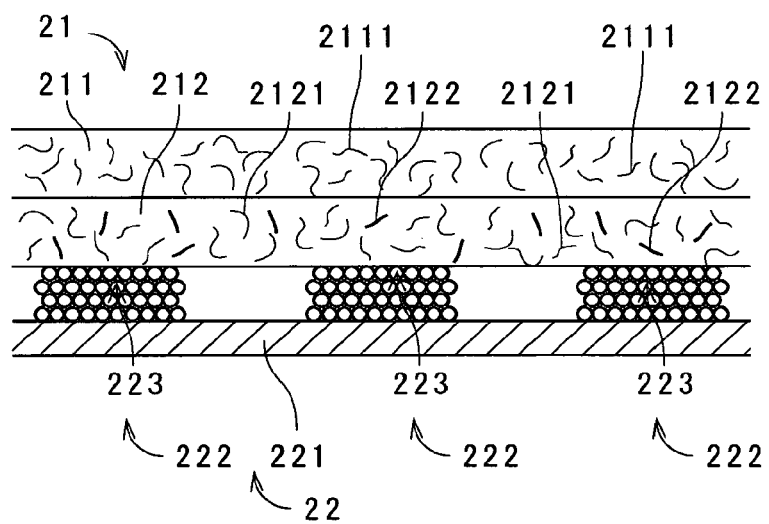
FIG. 3 is an enlarged cross-sectional view showing part of a top sheet and an absorbent core.

FIG. 3 is an enlarged cross-sectional view showing part of the top sheet 21 and the absorbent core 22. The top sheet 21 is a laminated body of two nonwoven fabrics as described above, and a nonwoven fabric 212 of the top sheet 21 (i.e., the nonwoven fabric 212 is opposed to the absorbent core 22 and is a lower nonwoven fabric 212 of the top sheet 21 in FIG. 3) is referred to as a "top sheet lower part 212" and a nonwoven fabric 211 positioned on the top sheet lower part 212 (i.e., an upper nonwoven fabric 211 of the top sheet 21 in FIG. 3) is referred to as a "top sheet upper part 211" in the following description. As shown in FIG. 3, the top sheet lower part 212 contacts with the high absorbent resin powder 223 forming the high absorbent resin layers 222 of the absorbent core 22. In FIG. 3, each of particles of the high absorbent resin powder 223 is depicted as larger than it actually is, for convenience of illustration. Hydrophilic fibers included in the top sheet 21 are shown by thick solid lines, and hydrophobic fibers are shown by thin solid lines (the same is applied in FIGS. 4 and 6).

The top sheet lower part 212 is made of hydrophilic fibers 2122 having water retention characteristics, the hydrophilic fibers 2122 being natural fibers and/or regenerated fibers (i.e., being at least one of natural fibers and regenerated fibers), and hydrophobic fibers 2121 which are synthetic fibers. The ratio of the hydrophilic fibers 2122 included in the top sheet lower part 212 is preferably equal to or larger than 25% by weight and equal to or smaller than 40% by weight. As the hydrophilic fibers 2122 included in the top sheet lower part 212, one or a plurality of types of fibers out of plant natural fibers such as cotton, pulp and hemp, animal natural fibers such as silk and wool, or regenerated fibers (also called semisynthetic fibers) such as rayon and acetate rayon are used.

As the hydrophobic fibers 2121 included in the top sheet lower part 212, synthetic fiber such as polypropylene (PP), polyethylene (PE), polyethylene terephthalate (PET), polyamide, polyurethane or acrylic, on which hydrophilic treatment is performed with a surfactant or the like, is used. In the top sheet lower part 212, composite fibers of the above synthetic fibers which are formed in a sheath-core structure, a sea-island structure, a divided structure or the like may be used as the hydrophobic fibers 2121. The hydrophilic treatment on the hydrophobic fibers 2121 may be performed on fibers before being formed as the top sheet lower part 212 or may be performed on fibers after being formed in a sheet form as the top sheet lower part 212 (the same is applied to the top sheet upper part 211). The fineness of the hydrophobic fibers 2121 included in the top sheet lower part 212 is preferably more than 3.0 decitex and more preferably, equal to or smaller than 7.0 decitex. The length of the hydrophobic fibers 2121 is preferably equal to or larger than 2.0 mm and equal to or smaller than 15.0 mm.

A ratio of hydrophilic fibers by weight in the top sheet upper part 211 is lower than that in the top sheet lower part 212, and the top sheet upper part 211 is made of only hydrophobic fibers 2111 which are synthetic fibers in the present preferred embodiment. As the hydrophobic fibers 2111 included in the top sheet upper part 211, one or a plurality of types of fibers (i.e., composite fibers) out of synthetic fibers such as polypropylene (PP), polyethylene (PE), polyethylene terephthalate (PET), polyamide, polyurethane and acrylic, are used similarly to the top sheet lower part 212. Also in the top sheet upper part 211, the hydrophilic treatment is performed on the hydrophobic fibers 2111 with use of a surfactant or the like. The fineness of the hydrophobic fibers 2111 included in the top sheet upper part 211 is preferably equal to or smaller than 3.0 decitex and more preferably, equal to or larger than 1.0 decitex. The length of the hydrophobic fibers 2111 is preferably equal to or larger than 2.0 mm and equal to or smaller than 15.0 mm.

The weight per unit area of the whole top sheet 21 is preferably equal to or larger than 15 g/m$^2$ and equal to or smaller than 35 g/m$^2$ and more preferably, equal to or larger than 20 g/m$^2$ and equal to or smaller than 30 g/m$^2$. The ratio between the weights per unit area of the top sheet upper part 211 and the top sheet lower part 212 is preferably 1:1 to 7:3. In the top sheet 21, for example, the weights per unit area of the whole top sheet 21, the top sheet upper part 211 and the top sheet lower part 212 are 22 g/m$^2$, 13 g/m$^2$ and 9 g/m$^2$, respectively, and the weights per unit area of the hydrophobic fibers 2121 and the hydrophilic fibers 2122 included in the top sheet lower part 212 are 6.6 g/m$^2$ and 2.4 g/m$^2$, respectively. For example, the weights per unit area of the whole top sheet 21, the top sheet upper part 211 and the top sheet lower part 212 are 22 g/m$^2$, 11 g/m$^2$ and 11 g/m$^2$, respectively, and the weights per unit area of the hydrophobic fibers 2121 and the hydrophilic fibers 2122 included in the top sheet lower part 212 are 7 g/m$^2$ and 4 g/m$^2$, respectively.

Manufacturing of the top sheet upper part 211 and the top sheet lower part 212 in the top sheet 21 may be performed by various manufacturing methods of nonwoven fabric, such as the air-laying method, the spunbond method, the meltblown method, the air-through method, the point bond method, the spunlace method, the needle punch method, and the chemical bond method. The air-laying method here is a method where a mixture of fibers and gas is ejected from one side of a breathable material and the gas is sucked from the other side of the breathable material to form fiber layers on the breathable material. By the method, it is possible to easily form a nonwoven fabric which is a mixture of a plurality of types of fibers. By using another nonwoven fabric as the above breathable material, it is possible to form a laminated body of nonwoven fabrics easily and rapidly. Further, by using nonwoven fabrics formed by different manufacturing methods as the above breathable material, it is possible to form a laminated body of nonwoven fabrics formed by different manufacturing methods easily and rapidly.

In manufacturing of the top sheet 21, it is preferable that the top sheet lower part 212 which is the lowest nonwoven fabric of the top sheet 21 is formed by the air-laying method. It is more preferable that the whole top sheet 21 (i.e., the laminated body of nonwoven fabrics which are formed by the top sheet upper part 211 and the top sheet lower part 212) is formed by the air-laying method. In the present preferred embodiment, the whole top sheet 21 is formed by the air-laying method.

As discussed above, since the absorbent core 22 includes 40% by weight or more of the high absorbent resin powder 223 in the absorbent product 1, it is possible to slim down the absorbent core 22 while keeping a sufficient amount of absorption (i.e., an amount of moisture which can be absorbed and retained), to thereby achieve slimming down of the absorbent product 1. In a case where the absorbent core 22 includes 50% by weight or more of the high absorbent resin powder 223, further slimming down of the absorbent core 22 and the absorbent product 1 is achieved.

In the top sheet 21, since the top sheet lower part 212 contacting the high absorbent resin powder 223 in the absorbent core 22 includes the hydrophilic fibers 2122 having water retention characteristics, moisture such as excreted urine is temporarily retained in the top sheet lower part 212 before reaching the absorbent core 22 and rapidly disperses in a range facing the absorbent core 22 of the top sheet lower part 212. As a result, it is possible to prevent concentration of large amounts of moisture in a portion close to a urination portion and the like of the absorbent core 22 and delay of absorption of the moisture, and even the absorbent core 22 in which moisture is absorbed by the high absorbent resin powder 223 whose absorption speed is relatively smaller than pulp and the like, can surely absorb moisture in excrement. With this operation, it is possible to prevent moving back of the moisture from the absorbent core 22 to the wearer through the top sheet 21.

In the absorbent product 1, since the top sheet lower part 212 which is a part of the top sheet 21 is used as a member for temporarily retaining the moisture before reaching the absorbent core 22 and rapidly dispersing the moisture, it is possible to simplify the structure of the absorbent product 1 as compared to the case where the above member is formed separately from the top sheet 21 and disposed between the top sheet 21 and the absorbent core 22. With this operation, manufacturing of the absorbent product 1 becomes easier and the manufacturing cost of the absorbent product 1 is reduced.

Since the ratio of the hydrophilic fibers by weight in the top sheet upper part 211 to come into contact with the wearer is lower than that in the top sheet lower part 212, the moisture is hard to be temporarily retained in the top sheet upper part 211 as compared with the top sheet lower part 212 and it is possible to make a surface of the top sheet 21 dry, and to improve feel of the top sheet 21 (especially, the feel from immediately after moisture or the like is excreted to when most of the moisture is absorbed by the absorbent core 22).

In the top sheet 21, since the top sheet lower part 212 includes 25% by weight or more of the hydrophilic fibers 2122, temporal retainment and rapid dispersion of the moisture by the top sheet lower part 212 is achieved more reliably. Since the hydrophilic fibers 2122 included in the top sheet lower part 212 is equal to or smaller than 40% by weight, it is possible to prevent temporarily excessive retainment of the moisture in the top sheet lower part 212, and to prevent moving back of the moisture from the top sheet 21 to the wearer.

The top sheet upper part 211 does not include hydrophilic fibers and is made of only the hydrophobic fibers 2111, and it is therefore possible to easily manufacture the top sheet upper part 211, the top sheet 21 and the absorbent product 1, and to prevent temporal retainment of the moisture in the top sheet upper part 211 and further improve feel of the top sheet 21.

As discussed above, the top sheet 21 is the laminated body of the two nonwoven fabrics which is the nonwoven fabric to be the top sheet lower part 212 including the hydrophilic fibers 2122 and the nonwoven fabric to be the top sheet upper part 211 made of only the hydrophobic fibers 2111. With this operation, formation of the top sheet 21 and the absorbent product 1 having the top sheet 21 can be easier.

In the top sheet 21, the top sheet lower part 212 mainly includes the hydrophobic fibers 2121 whose fineness is more than 3.0 decitex and is equal to or smaller than 7.0 decitex, and the top sheet upper part 211 mainly includes the hydrophobic fibers 2111 whose fineness is equal to or larger than 1.0 decitex and equal to or smaller than 3.0 decitex. As described, by making the relatively thick hydrophobic fibers 2121 included in the top sheet lower part 212 which contacts the absorbent core 22, the moisture included in the top sheet lower part 212 can more smoothly reach the absorbent core 22. By making the relatively thin hydrophobic fibers 2111 included in the top sheet upper part 211 to come into contact with the wearer, it is possible to enhance the flexibility of the top sheet upper part 211 and further improve feel of the top sheet 21.

The above absorbent core 22 has a structure in which the high absorbent resin powder 223 is bonded on the sheet-like supporting member 221 and relatively bulky pulp fibers are not included. With this operation, it is possible to achieve further slimming down of the absorbent core 22 and to suppress twist and deformation of the absorbent core 22 caused by movement of the wearer, and as a result, the absorbent core 22 can absorb the moisture of excrement more reliably. Since the mount 24 overlapping with the whole of the absorbent core 22 is provided between the absorbent core 22 and the back sheet 23, it is possible to further suppress twist and deformation of the absorbent core 22.

In the absorbent core 22, the weight per unit area of the supporting member 221 is equal to or larger than $10 \text{ g/m}^2$ and thereby, the strength of the supporting member 221 is more increased, and handling of the supporting member 221 in manufacturing the absorbent core 22 and handing of the absorbent core 22 in manufacturing the absorbent product 1 become easier. Since the weight per unit area of the supporting member 221 is equal to or smaller than $100 \text{ g/m}^2$, it is possible to further enhance the flexibility of the absorbent core 22 and further provide the wearer with comfortable feeling in wearing the absorbent product 1.

In the absorbent core 22, the high absorbent resin powder 223 is applied on the supporting member 221 in stripe pattern, and the moisture rapidly disperses in the longitudinal direction of the absorbent product 1 on the areas where the high absorbent resin powder 223 does not exist (i.e., the areas are groove portions between the high absorbent resin layers 222 arranged in stripe pattern). With this operation, it is possible to more reliably prevent partial concentration of the moisture in the absorbent core 22 and delay of absorption of the moisture, and to absorb the moisture of excrement more reliably.

In manufacturing of the top sheet 21, by using the air-laying method, the hydrophilic fibers 2122 and the hydrophobic fibers 2121 are almost uniformly mixed and the top sheet lower part 212 can be formed easily and rapidly. It is also possible to easily and rapidly form the whole top sheet 21 which is a laminated body of nonwoven fabrics whose types are different from each another, by the air-laying method.

Figure 4:
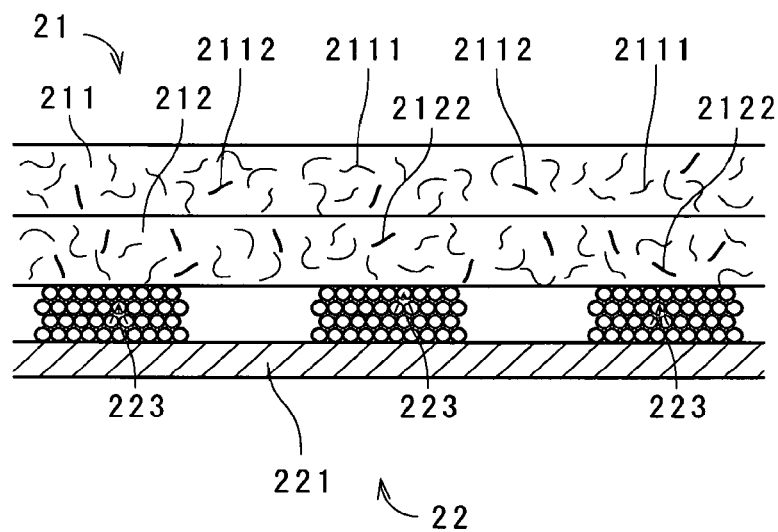
FIG. 4 is an enlarged cross-sectional view showing part of a top sheet and an absorbent core in an absorbent product in accordance with the second preferred embodiment.

Next discussion will be made on an absorbent product in accordance with the second preferred embodiment of the present invention. FIG. 4 is an enlarged cross-sectional view showing part of a top sheet 21 and an absorbent core 22 in the absorbent product in accordance with the second preferred embodiment. As shown in FIG. 4, the absorbent product according to the second preferred embodiment has the same structure as that in the absorbent product 1 shown in FIGS. 1 to 3 excepting a top sheet upper part 211 in the top sheet 21 includes hydrophilic fibers 2112 similar to a top sheet lower part 212. The constituent elements identical to those in the absorbent product 1 are represented by the same reference signs in the following description.

In the absorbent product according to the second preferred embodiment, the top sheet upper part 211 in the top sheet 21 includes the hydrophobic fibers 2111 which are synthetic fibers with the hydrophilic treatment and the hydrophilic fibers 2112 having water retention characteristics, the hydrophilic fibers 2112 being natural fibers and/or regenerated fibers. The ratio of the hydrophilic fibers 2112 included in the top sheet upper part 211 is equal to or smaller than 15% by weight.

Similarly to the first preferred embodiment, the top sheet lower part 212 includes the hydrophilic fibers 2122 whose ratio is equal to or larger than 25% by weight and equal to or smaller than 40% by weight. The absorbent core 22 has the sheet-like supporting member 221 and the high absorbent resin powder 223 bonded on a main surface of the supporting member 221, the main surface being opposed to the top sheet 21. The ratio of the high absorbent resin powder 223 included in the absorbent core 22 is equal to or larger than 40% by weight (more preferably, equal to or larger than 50% by weight), similarly to the first preferred embodiment.

In the absorbent product according to the second preferred embodiment, similarly to the first preferred embodiment, since the absorbent core 22 includes 40% by weight or more of the high absorbent resin powder 223, it is possible to slim down the absorbent core 22 while keeping a sufficient amount of absorption to thereby achieve slimming down of the absorbent product. The top sheet lower part 212 contacting the high absorbent resin powder 223 in the absorbent core 22 includes the hydrophilic fibers 2122 having water retention characteristics and therefore, moisture of excrement can be absorbed in the absorbent core 22 more reliably and the structure of the absorbent product can be simplified. The ratio of the hydrophilic fibers by weight in the top sheet upper part 211 to come into contact with the wearer is lower than that in the top sheet lower part 212 and it is possible to make a surface of the top sheet 21 dry, and to improve feel of the top sheet 21.

In the absorbent product according to the second preferred embodiment, since the top sheet upper part 221 especially includes the hydrophilic fibers 2112 whose ratio is equal to or smaller than 15% by weight and moisture such as urine can rapidly disperse in the top sheet upper part 211, it is possible to more reliably prevent partial concentration of the moisture in the absorbent core 22 and delay of absorption of the moisture, and to absorb the moisture of excrement in the absorbent core 22 more reliably. It is also possible to prevent temporarily excessive retainment of the moisture in the top sheet upper part 211, and to thereby prevent moving back of the moisture from the top sheet 21 to the wearer.

Figure 5:
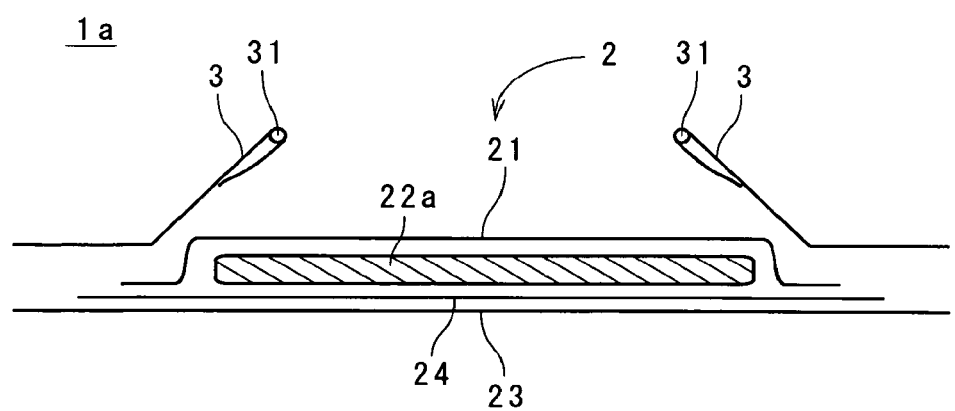
FIG. 5 is a cross-sectional view of an absorbent product in accordance with the third preferred embodiment.
Figure 6:
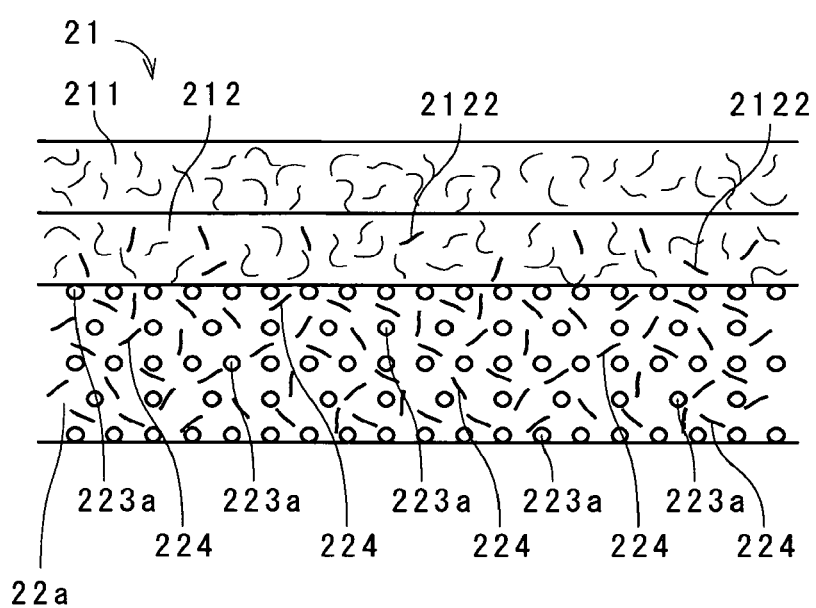
FIG. 6 is an enlarged cross-sectional view showing part of a top sheet and an absorbent core.

Next, discussion will be made on an absorbent product in accordance with the third preferred embodiment of the present invention. FIG. 5 is a cross-sectional view of an absorbent product 1a according to the third preferred embodiment and corresponds to FIG. 2. As shown in FIG. 5, the absorbent product 1a has the same structure as that in the absorbent product 1 shown in FIGS. 1 to 3 excepting the absorbent product 1a has an absorbent core 22a whose structure is different from the absorbent core 22 shown in FIG. 2. The constituent elements identical to those in the absorbent product 1 are represented by the same reference signs in the following description. FIG. 6 is an enlarged cross-sectional view showing part of the top sheet 21 and the absorbent core 22a in the absorbent product 1a and corresponds to FIG. 3.

The absorbent core 22a in the absorbent product 1a shown in FIG. 6 has 40% by weight or more (more preferably, 50% by weight or more) of high absorbent resin powder particles 223a and hydrophilic fibers 224 having water retention characteristics. In the absorbent core 22a, the high absorbent resin powder particles 223a disperse in a cluster of the thick sheet-like (so-called mat-like) hydrophilic fibers 224, and the high absorbent resin powder particles 223a exposed on a surface of the cluster of the hydrophilic fibers 224, the surface being opposed to the top sheet 21, contact with the top sheet lower part 212 in the top sheet 21.

As the hydrophilic fibers 224 included in the absorbent core 22a, one or a plurality of types of fibers out of plant natural fibers such as cotton, pulp and hemp, animal natural fibers such as silk and wool, or regenerated fibers (also called semisynthetic fibers) such as rayon and acetate rayon are used similarly to the hydrophilic fibers 2122 included in the top sheet lower part 212 in the absorbent product 1 according to the first preferred embodiment. In the present preferred embodiment, pulp fibers are used as the hydrophilic fibers 224 and the weight per unit area of the hydrophilic fibers 224 is equal to or larger than 80 g/m$^2$ and equal to or smaller than 200 g/m$^2$.

In the absorbent product 1a, similarly to the first preferred embodiment, since the absorbent core 22a includes 40% by weight or more of the high absorbent resin powder particles 223a, it is possible to slim down the absorbent core 22a while keeping a sufficient amount of absorption to thereby achieve slimming down of the absorbent product 1a. The top sheet lower part 212 contacting the high absorbent resin powder particles 223a in the absorbent core 22a includes the hydrophilic fibers 2122 having water retention characteristics and therefore, moisture of excrement can be absorbed in the absorbent core 22a more reliably and the structure of the absorbent product 1a can be simplified. The ratio of the hydrophilic fibers by weight in the top sheet upper part 211 to come into contact with the wearer is lower than that in the top sheet lower part 212 and it is possible to make a surface of the top sheet 21 dry, and to improve feel of the top sheet 21.

In the absorbent product 1a according to the third preferred embodiment, the absorbent core 22a especially includes the hydrophilic fibers 224 having water retention characteristics and the thickness of the absorbent core 22a becomes thicker in some degree as compared with the absorbent product 1 according to the first preferred embodiment. However, since an absorption speed of moisture in the absorbent core 22a is increased, it is possible to absorb the moisture of excrement in the absorbent core 22a more rapidly and more reliably.

In the absorbent core 22a, since the weight per unit area of the hydrophilic fibers 224 is equal to or larger than 80 g/m$^2$, uniformity of the density in the absorbent core 22a are more increased, the high absorbent resin powder particles 223a are reliably held by the hydrophilic fibers 224 and absorption of moisture by the absorbent core 22a is performed more reliably. The weight per unit area of the hydrophilic fibers 224 is equal to or smaller than 200 g/m$^2$ and it is therefore possible to further enhance the flexibility of the absorbent core 22a and further provide the wearer with comfortable feeling in wearing the absorbent product 1a.

Though the preferred embodiments of the present invention have been discussed above, the present invention is not limited to the above-discussed preferred embodiments, but allows various variations.

For example, the top sheet 21 may be a laminated body of three or more nonwoven fabrics, and at least the lowest nonwoven fabric out of the plurality of nonwoven fabrics is included in the top sheet lower part 212 including the above hydrophilic fibers 2122 which are natural fibers and/or regenerated fibers and at least the uppermost nonwoven fabric is included in the top sheet upper part 211 whose ratio of the hydrophilic fibers by weight is lower than the top sheet lower part 212. Even in this case, since the top sheet upper part 211 and the top sheet lower part 212 are formed by separate nonwoven fabrics, it is possible to easily form the top sheet 21 and an absorbent product having the top sheet 21.

The top sheet 21 is not necessarily a laminated body of a plurality of nonwoven fabrics but may be one nonwoven fabric. Also in this case, a lower part (i.e., a part opposed to an absorbent core) of the nonwoven fabric is the top sheet lower part 212 including the hydrophilic fibers 2122 having water retention characteristics and the upper part (i.e., a part opposed to the wearer) of the nonwoven fabric is the top sheet upper part 211 whose ratio of the hydrophilic fibers by weight is lower than the top sheet lower part 212. Thus, it is possible to absorb moisture of excrement in the absorbent core more reliably and to improve feel of the top sheet 21.

In the absorbent products according to the first and second preferred embodiments, a plurality of absorbent cores 22 may be laminated between the top sheet 21 and the back sheet 23, as long as the top sheet lower part 212 contacts with the high absorbent resin powder 223 included in the absorbent core 22. Also in the absorbent product 1a according to the third preferred embodiment, a plurality of absorbent cores 22a may be laminated and in this case, liquid-pervious nonwoven fabrics, tissue papers or the like may be disposed between the plurality of absorbent cores 22a.

In the absorbent product 1a, deformation of the absorbent core 22a may be suppressed by applying the hot melt adhesive onto a surface of the absorbent core 22a in a fibrous pattern. In the surface of the absorbent core 22a, a whole area excluding an area opposed to the top sheet 21 or a part of the whole area may be covered with a liquid-pervious nonwoven fabric, a tissue paper or the like, and deformation of the absorbent core 22a is thereby suppressed. In order to suppress deformation of the absorbent core 22a in absorbing moisture, hydrophobic fibers with the hydrophilic treatment may be mixed with the cluster of the hydrophilic fibers 224 in the absorbent core 22a.

The absorbent products according to the above preferred embodiments may be used as a sanitary napkin for receiving excrement such as menstrual blood from a wearer or may be used as a pad part of a panty liner, as well as an auxiliary absorbent pad. The absorbent product may be used as a pants-type disposal diaper which has a waist opening at an upper end and a pair of leg openings on a lower part or an open-type disposal diaper where a portion located on a stomach side of a wearer and a portion located on a back side are fastened around waistline of the wearer in wearing the disposal diaper.

While the invention has been shown and described in detail, the foregoing description is in all aspects illustrative and not restrictive. It is therefore understood that numerous modifications and variations can be devised without departing from the scope of the invention.

This application claims priority benefit under 35 U.S.C. Section 119 of Japanese Patent Application No. 2007-164672 filed in the Japan Patent Office on Jun. 22, 2007, the entire disclosure of which is incorporated herein by reference.

What is claimed is:

1. An absorbent product for receiving excrement from a wearer, the absorbent product comprising:
    an absorbent core which includes 40% by weight or more of high absorbent resin powder and hydrophilic fibers having water retention characteristics, said high absorbent resin powder being dispersed in a cluster of said hydrophilic fibers in said absorbent core;
    a top sheet which is made of nonwoven fabric covering an upper surface of said absorbent core, said top sheet comprising a top sheet lower part and a top sheet upper part; and
    a back sheet covering a lower surface of said absorbent core,
    wherein said top sheet lower part includes hydrophilic fibers having water retention characteristics, said hydrophilic fibers being natural fibers and/or regenerated fibers,
    wherein said top sheet upper part is positioned on said top sheet lower part, a ratio of said hydrophilic fibers by weight in said top sheet upper part being lower than that in said top sheet lower part, and wherein said top sheet lower part directly contacts a part of said high absorbent resin powder exposed on a surface of said cluster of said hydrophilic fibers, said surface being opposed to said top sheet.

2. The absorbent product according to claim 1, wherein said top sheet is a single nonwoven fabric.

3. The absorbent product according to claim 1, wherein a ratio of said hydrophilic fibers included in said top sheet lower part is equal to or larger than 25% by weight and equal to or smaller than 40% by weight.

4. The absorbent product according to claim 1, wherein a ratio of said hydrophilic fibers included in said top sheet upper part is equal to or smaller than 15% by weight.

5. The absorbent product according to claim 1, wherein said top sheet upper part is made of only hydrophobic fibers which are synthetic fibers.

6. The absorbent product according to claim 1, wherein said top sheet is a laminated body of a plurality of nonwoven fabrics, said top sheet lower part includes a lowest nonwoven fabric of said plurality of nonwoven fabrics, and said top sheet upper part includes an uppermost nonwoven fabric of said plurality of nonwoven fabrics.

7. The absorbent product according to claim 6, wherein said top sheet is a laminated body of two nonwoven fabrics.

8. The absorbent product according to claim 6, wherein said lowest nonwoven fabric of said top sheet is formed by an air-laying method.

9. The absorbent product according to claim 8, wherein said plurality of nonwoven fabrics are formed by said air-laying method.

10. The absorbent product according to claim 1, wherein said top sheet lower part includes hydrophobic fibers which are synthetic fibers whose fineness is more than 3.0 decitex and equal to or smaller than 7.0 decitex, and said top sheet upper part includes hydrophobic fibers which are synthetic fibers whose fineness is equal to or larger than 1.0 decitex and equal to or smaller than 3.0 decitex.

11. The absorbent product according to claim 1, the absorbent product further comprising a sheet member which overlaps with a whole of said absorbent core between said absorbent core and said back sheet.

* * * * *